United States Patent [19]

Buzzese et al.

[11] Patent Number: 4,640,275
[45] Date of Patent: Feb. 3, 1987

[54] HEAD RESTRAINT FOR BACKBOARDS

[76] Inventors: Vincent J. Buzzese, 324 Greenbrier Rd., Sunbury, Ohio 43074; Mario Dohnert, Jr., 873 Mike Ct., Westerville, Ohio 43081

[21] Appl. No.: 719,506

[22] Filed: Apr. 3, 1985

[51] Int. Cl.$^4$ ............................................. A61F 5/37
[52] U.S. Cl. ..................................... 128/133; 5/437; 269/328
[58] Field of Search ..................... 128/76 R, 133, 134, 128/135; 269/322, 328; 5/434, 437, 82 R

[56] References Cited

U.S. PATENT DOCUMENTS

| | | | |
|---|---|---|---|
| 1,688,382 | 10/1928 | Ghrist | 269/328 |
| 2,535,559 | 12/1950 | Wolf | 269/328 |
| 3,650,523 | 3/1972 | Darby, Jr. | 269/328 |
| 3,897,777 | 8/1975 | Morrison | 128/133 |
| 4,058,112 | 11/1977 | Johnson | 128/133 X |
| 4,321,718 | 3/1982 | Chern | 5/437 |
| 4,526,355 | 7/1985 | Moore et al. | 269/328 |
| 4,571,757 | 2/1986 | Zolecki | 5/82 R |

Primary Examiner—Richard T. Stouffer
Attorney, Agent, or Firm—Biebel, French & Nauman

[57] ABSTRACT

This device serves to immobilize the head and neck area of people who have obvious or suspected cervical trauma. Primarily, it consists of a metal frame with clear plastic side plates, for preventing the movement of the user's head, and it also includes a channel with a set screw, for holding the frame of the device to one end of a backboard.

4 Claims, 3 Drawing Figures

HEAD RESTRAINT FOR BACKBOARDS

This invention relates to medical restraining devices, and more particularly, to a head restraint for backboards.

The principal object of this invention is to provide a head restraint for backboards, which will be unique in design, for immobilizing the head and neck area of people who have obvious or suspected cervical trauma.

Another object of this invention is to provide a head restraint for backboards, which will be adjustable for different head sizes for aiding in the immobilization process, and plastic encased foam pads will be employed under the individual's head and between their ears, and also the inner sides of the device.

A further object of this invention is to provide a head restraint for backboards, which will include a Velcro strap for placement across the forehead and from side to side of the device, as a final step for securing the device to the head, thus further effecting immobilization of the cervical area.

Other objects are to provide a head restraint for backboards, which is simple in design, inexpensive to manufacture, rugged in construction, easy to use, and efficient in operation.

These, and other objects, will be readily evident, upon a study of the following specification, and the accompanying drawings, wherein.

Figure 1:
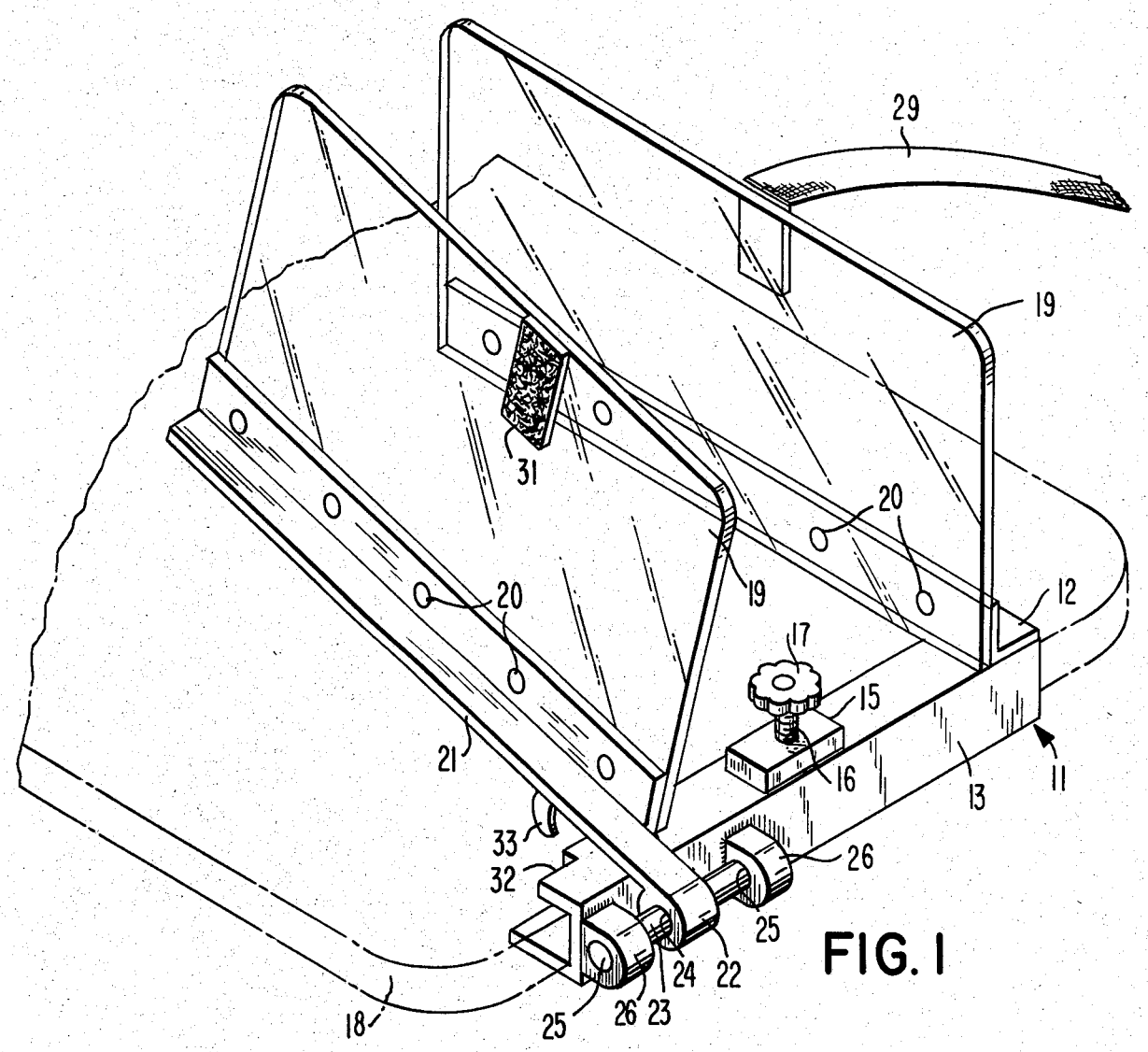
FIG. 1 is a fragmentary perspective view of the present invention, showing the headboard fragmentary and in phantom lines.
Figures 2, 3:
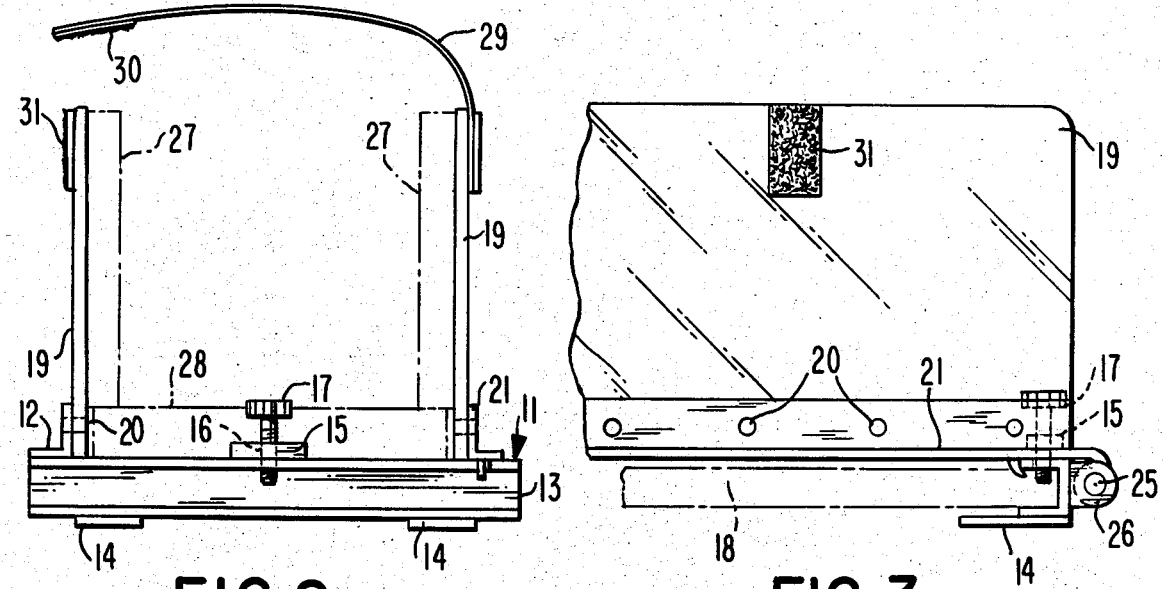
FIG. 2 is a front elevational view of FIG. 1, shown on a smaller scale, and illustrating foam pads in phantom lines.
FIG. 3 is a side view of FIG. 2.

According to this invention, a device 10 is shown to include an aluminum frame 11, having an angle rail 12 fixedly and non-adjustably secured in a suitable manner, to the top leg portion of a "U"-shaped channel 13 at one end, and support plates 14 are suitably fixedly secured near the ends of the bottom leg portion of channel 13. A reinforcement plate 15 is fixedly secured to the center portion of the top surface of the top leg portion of channel 13, and includes a threaded opening 16 therein, which receives a knobbed set screw 17, for tightening channel 13 to one end of backboard 18, thus rendering device 10 secured thereto. A pair of clear side plates 19 are provided and one is fixedly secured to the upright portion of rail 12 by a plurality of spaced rivet fasteners 20. The other of the pair is similarly secured to the upright portion of an arm 21, which includes an eye portion 22. The side plates 19 serve to prevent side movement of the head of the person using device 10, and the eye portion 22 freely receives a pin or shaft 23 within its opening 24. The ends of pin 23 are force fitted within openings 25 of a pair of projections 26, which are spaced apart and welded to channel 13 at its rear to form support means for the other of the pair of side plates 19. Arm 21 is pivotally elevatable, and is also adjustable horizontally on pin 23, so as to help compensate for different head sizes.

A pair of plastic covered foam pads 27 are provided, and each is placed against the inside face of the side plates 19, and are employed in cooperation with a similar bottom pad 28, for providing comfort to the user's head. A hook-loop or Velcro fastener strap 29 is also provided and is fixedly secured at one end, to the rear top outside portion of one of the side plates 19, for extending across the top of the device 10, for engaging with the forehead of the user, for additional restraint.

A hook-loop or Velcro strip 30 is fixedly secured in a suitable manner to one end of strap 29, and a similar and mating hook-loop or Velcro strip 31 is fixedly secured in a suitable manner, to the outside of the side plate 19 that is pivotally and horizontally adjustable, so as to engage with each other adjustably. A cut-out opening 32 is provided in the top portion of one end of channel 13, and an arcuate hook 33 is suitably welded or otherwise secured to the bottom of arm 21, so as to engage with the top longitudinal edge of channel 13 and thereby form stabilizing means for preventing arm 21 from pivoting upward after adjustment to the size of an individual's head. When it is desired to pivot arm 21 upward, arm 21 is urged towards the end of the channel 13, and the cut-out 32 causes the hook 33 to be free for the elevation or pivoting of arm 21.

In use, channel 13 is placed in engagement with the end of the backboard 18, and the set screw 17 is tightened down thereon, which renders device 10 secure to backboard 18. The user than places his head on the backboard 18, between the side plates 19, after pad 28 is in place. The pads 27 are then inserted alongside the user's head, and the Velcro fastener strap 29 is brought across the user's forehead, and secured in the manner known in the art.

While various changes may be made in the detail construction, it is understood that such changes will be within the spirit and scope of the present invention, as is defined by the appended claims.

What we now claim is:

1. A head restraining device for use with a backboard to immobilize the head and neck area of a person supported upon the backboard and apparently suffering cervical trauma, said head restraining device comprising:
   a frame removably securable to one end of the backboard;
   a pair of side plates, one of said side plates being fixedly and nonadjustably secured to one end of said frame to extend in a generally perpendicular orientation over the backboard when said frame is secured to the backboard;
   support means secured to the other end of said frame opposite to said one end, said support means supporting the other of said pair of side plates for pivotal movement about a horizontal axis toward and away from the backboard and horizontal movement along said axis and along a portion of said frame whereby said other side plate can be pivoted into a generally perpendicular orientation over the backboard and horizontally moved toward said fixedly secured side plate to adjust said head restraining device for different head sizes; and
   a fastener strap having one end fixedly secured to one of said pair of side plates and the other end adapted to be removably secured to the other of said pair of side plates, said fastener strap being positioned relative to said side plates such that it is adapted to be generally aligned with the forehead of a person supported upon the backboard when the strap is fastened to secure a person's head between said pair of side plates.

2. A head restraining device as claimed in claim 1 wherein said support means comprises a pair of projections secured to said frame and supporting a shaft therebetween, the other of said pair of side plates being mounted to include an eye portion receiving said pin and being pivotally movable about said pin and horizontally movable along said pin with said pin defining said horizontal axis.

3. A head restraining device as claimed in claim 2 further comprising stabilizing means for preventing pivotal movement of the other of said pair of side plates after it is horizontally moved to adjust said head restraining device for a given head size.

4. A head restraining device as claimed in claim 3 wherein said stabilizing means comprises a hook secured to the other of said pair of side plates and engageable with said frame, said frame including a cut-out opening for passing said hook to permit pivotable movement when said hook is aligned with said cut-out opening.

* * * * *

UNITED STATES PATENT AND TRADEMARK OFFICE
CERTIFICATE OF CORRECTION

PATENT NO. : 4,640,275

DATED : February 3, 1987

INVENTOR(S) : Vincent J. Bruzzese and Mario Dohnert, Jr.

It is certified that error appears in the above—identified patent and that said Letters Patent is hereby corrected as shown below:

On the face of the patent "Buzzese et al." should read
--Bruzzese et al.--; and
"[76] Inventors: Vincent J. Buzzese" should read
--[76] Inventors: Vincent J. Bruzzese--.

Signed and Sealed this

Twenty-first Day of April, 1987

Attest:

DONALD J. QUIGG

Attesting Officer

Commissioner of Patents and Trademarks